US009229032B2

(12) United States Patent
Ide et al.

(10) Patent No.: US 9,229,032 B2
(45) Date of Patent: Jan. 5, 2016

(54) CURRENT SENSOR (71) Applicant: ALPS GREEN DEVICES CO., LTD., Tokyo (JP)

(72) Inventors: Yosuke Ide, Niigata-ken (JP); Masamichi Saito, Niigata-ken (JP); Akira Takahashi, Niigata-ken (JP); Kenji Ichinohe, Niigata-ken (JP); Yoshihiro Nishiyama, Niigata-ken (JP)

(73) Assignee: ALPS GREEN DEVICES CO., LTD., Tokyo (JP)

( * ) Notice: Subject to any disclaimer, the term of this patent is extended or adjusted under 35 U.S.C. 154(b) by 343 days.

(21) Appl. No.: 13/856,345

(22) Filed: Apr. 3, 2013

(65) Prior Publication Data

US 2013/0221998 A1 Aug. 29, 2013

Related U.S. Application Data (63) Continuation of application No. PCT/JP2011/073220, filed on Oct. 7, 2011.

(30) Foreign Application Priority Data

Nov. 1, 2010 (JP) .................................. 2010-245291

(51) Int. Cl.
*G01R 27/08* (2006.01)
*G01R 19/00* (2006.01)
*B82Y 25/00* (2011.01)
*G01R 15/20* (2006.01)
*G01R 33/09* (2006.01)
*H01L 43/08* (2006.01)
*B82Y 5/00* (2011.01)
(Continued)

(52) U.S. Cl.
CPC ................. *G01R 19/00* (2013.01); *B82Y 25/00* (2013.01); *G01R 15/205* (2013.01);
(Continued)

(58) Field of Classification Search
CPC ........ B82Y 5/00; G11B 3/00; G11B 2209/00; G11B 2220/00; G01R 1/00; H01L 21/00; H01L 2221/00; H01L 2223/00; H01L 2924/00; H01L 2925/00; H01F 1/00
See application file for complete search history.

(56) References Cited

U.S. PATENT DOCUMENTS 6,028,786 A * 2/2000 Nishimura .................... 365/173
6,512,660 B1 * 1/2003 Li .......................... B82Y 10/00
360/324

(Continued)

FOREIGN PATENT DOCUMENTS

JP 2002-71775 3/2002
JP 2006-66821 3/2006
(Continued)

OTHER PUBLICATIONS

Search Report dated Dec. 20, 2011 from International Application No. PCT/JP2011/073220.

*Primary Examiner* — Huy Q Phan
*Assistant Examiner* — Temilade Rhodes-Vivour
(74) *Attorney, Agent, or Firm* — Beyer Law Group LLP (57) ABSTRACT

A current sensor includes a magnetoresistive element that has a stripe shape and that has a sensing axis in a certain direction. The magnetoresistive element includes element portions that are disposed so as to be spaced apart from each other in a longitudinal direction of the stripe shape, and permanent magnet portions, each of which is disposed between adjacent ones of the element portions. Each element portion has a layered structure including a free magnetic layer whose magnetization direction is changed with respect to an external magnetic field, a non-magnetic intermediate layer, and a ferromagnetic pinned layer whose magnetization direction is pinned. The permanent magnet portion includes a hard bias layer, and an electrode layer that is disposed so as to cover the hard bias layer.

11 Claims, 8 Drawing Sheets (51) Int. Cl.
*G11B 3/00* (2006.01)
*H01F 1/00* (2006.01)

(52) U.S. Cl.
CPC ............. *G01R 33/093* (2013.01); *H01L 43/08*
(2013.01); *B82Y 5/00* (2013.01); *G11B 3/00*
(2013.01); *H01F 1/00* (2013.01)

(56) References Cited

U.S. PATENT DOCUMENTS

| | | | |
|---|---|---|---|
| 6,519,124 B1 * | 2/2003 | Redon | B82Y 10/00 360/321 |
| 6,885,527 B1 * | 4/2005 | Ju | G11B 5/29 29/603.1 |
| 7,859,258 B2 | 12/2010 | Sasaki et al. | |
| 2005/0237677 A1 | 10/2005 | Shimazawa et al. | |
| 2009/0002898 A1 * | 1/2009 | Childress et al. | 360/324.1 |
| 2010/0253330 A1 | 10/2010 | Sasaki et al. | |
| 2011/0007426 A1 * | 1/2011 | Qiu et al. | 360/313 |
| 2011/0227560 A1 * | 9/2011 | Haratani et al. | 324/117 R |

FOREIGN PATENT DOCUMENTS

| | | |
|---|---|---|
| JP | 2007-273528 | 10/2007 |
| JP | 2011-7673 | 1/2011 |

* cited by examiner

CURRENT SENSOR

CLAIM OF PRIORITY

This application is a Continuation of International Application No. PCT/JP2011/073220 filed on Oct. 7, 2011, which claims benefit of Japanese Patent Application No. 2010-245291 filed on Nov. 1, 2010. The entire contents of each application noted above are hereby incorporated by reference.

BACKGROUND OF THE INVENTION

1. Field of the Invention

The present invention relates to current sensors that measure the magnitude of a current, and more particularly, to a current sensor including magnetoresistive elements.

2. Description of the Related Art

Heretofore, in the fields of, for example, electric cars and solar batteries, a current sensor including magnetic detection devices which output an output signal due to an induction field caused by a measurement current has been used. An example of a magnetic detection device included in such a current sensor is a magnetoresistive element such as a giant magnetoresistive (GMR) element.

A GMR element has a basic film structure including an antiferromagnetic layer, a ferromagnetic pinned layer, a non-magnetic material layer, and a free magnetic layer. The ferromagnetic pinned layer is formed on the antiferromagnetic layer so as to be in contact with the antiferromagnetic layer, and has a magnetization direction that is pinned in a certain direction due to the exchange coupling magnetic field (Hex) which occurs between the antiferromagnetic layer and the ferromagnetic pinned layer. The free magnetic layer is stacked on the ferromagnetic pinned layer with the non-magnetic material layer (non-magnetic intermediate layer) interposed between the free magnetic layer and the ferromagnetic pinned layer, and has a magnetization direction which is changed due to the external magnetic field. In a current sensor including GMR elements, the current value of a measurement current is detected using electrical resistance values of the GMR elements which are changed depending on the relationship between the magnetization direction of the free magnetic layer which is changed due to application of the induction field caused by a measurement current and the magnetization direction of the ferromagnetic pinned layer. As a current sensor including GMR elements, a current sensor has been proposed in which a hard bias layer for applying a bias magnetic field to a free magnetic layer is formed to enhance the linear relationship (linearity) between the electrical resistance value of a GMR element and the intensity of the external magnetic field (for example, see Japanese Unexamined Patent Application Publication No. 2006-66821).

In such a current sensor, GMR elements are disposed so as to be oriented in the longitudinal direction of the stripe shape thereof and to be parallel to each other. Hard bias layers which also serve as an electrode are formed at the ends and the midpoint of each of the GMR elements in the longitudinal direction of the stripe shape. Each of the GMR elements is stacked on the hard bias layers, and is electrically connected with the adjacent GMR elements through the hard bias layers disposed at the ends of the GMR element.

To further improve the measurement accuracy in a current sensor, reduction in an output signal offset, reduction in gain variation, and improvement of the linearity of the output characteristics are required. In contrast, a current sensor including magnetoresistive elements has a problem in that an offset occurs in an output signal due to the hysteresis in the R-H curve for a magnetoresistive element. In the current sensor described in Japanese Unexamined Patent Application Publication No. 2006-66821, by applying a bias magnetic field from a hard bias layer to a free magnetic layer, the magnetization direction of the free magnetic layer is initialized so that the hysteresis is reduced.

However, in the current sensor described in Japanese Unexamined Patent Application Publication No. 2006-66821, the free magnetic layer of a GMR element is directly stacked on the hard bias layers. Therefore, in a contact portion which is in the free magnetic layer and which is in contact with a hard bias layer, the magnetization direction is strongly pinned due to the bias magnetic field from the hard bias layer. Even when the induction field from a measurement current operates, the magnetization direction is not changed, causing the contact portion to serve as a dead zone from which an output signal is not obtained. Thus, when a dead zone is present, there arises a problem in that the hysteresis is not sufficiently reduced.

SUMMARY OF THE INVENTION

The present invention is made in view of the above-described problems, and provides a current sensor which can reduce the hysteresis of a magnetoresistive element and which has high measurement accuracy.

A current sensor according to the present invention includes a magnetoresistive element that has a stripe shape and that has a sensing axis in a certain direction. The magnetoresistive element includes multiple element portions that are disposed so as to be spaced apart from each other in a longitudinal direction of the stripe shape, and multiple permanent magnet portions, each of which is disposed between adjacent ones of the element portions. Each of the element portions has a layered structure including a free magnetic layer whose magnetization direction is changed with respect to an external magnetic field, a non-magnetic intermediate layer, and a ferromagnetic pinned layer whose magnetization direction is pinned. The permanent magnet portion includes a hard bias layer that applies a bias magnetic field to the free magnetic layer, and an electrode layer that is disposed so as to cover the hard bias layer and that electrically connects adjacent ones of the element portions.

In this configuration, the bias magnetic field applied from the hard bias layer of a permanent magnet portion to the free magnetic layer of an element portion causes uniaxial anisotropy to be provided for the free magnetic layer of the element portion, and the structure in which a permanent magnet portion is formed between adjacent ones of the element portions causes the area in which the free magnetic layer is contact with the hard bias layer to be reduced. This enables a dead zone in the free magnetic layer to be reduced, resulting in a reduced hysteresis. Further, by providing each of the permanent magnet portions with an electrode layer, output signals from element portions are output via the electrode layers of the permanent magnet portions. Therefore, even when a permanent magnet portion is provided between adjacent ones of the element portions, parasitic resistance can be reduced, and variation which occurs in the zero-field resistance values (R0) and the temperature coefficients of resistance (TCR0) in a zero magnetic field among the magnetoresistive elements and which is caused by the parasitic resistance can be suppressed. Accordingly, a current sensor having high measurement accuracy can be achieved.

In the current sensor according to the present invention, it is preferable that an underlying layer be disposed between the hard bias layer of the permanent magnet portion and the free magnetic layer of the element portion.

In this configuration, the free magnetic layer and the hard bias layer are in contact with each other via the underlying layer. Therefore, the state in which the magnetization direction of the free magnetic layer is pinned due to the bias magnetic field from the hard bias layer can be suppressed, causing a dead zone in the current sensor to be reduced.

In the current sensor according to the present invention, it is preferable that the hard bias layer of the permanent magnet portion be disposed in a region in which the ferromagnetic pinned layer, the non-magnetic intermediate layer, and the free magnetic layer in the element portion of the magnetoresistive element are removed.

In the current sensor according to the present invention, it is preferable that the magnetoresistive element has a shape in which multiple long belt-like strips disposed so as to be oriented in the longitudinal direction of the stripe shape and to be parallel with each other be connected at the ends with connecting portions.

In the current sensor according to the present invention, it is preferable that, in the magnetoresistive element, a stripe width range from 2 μm to 9 μm. This configuration enables the hysteresis to be reduced.

In the current sensor according to the present invention, it is preferable that a pitch between the hard bias layers of the permanent magnet portions that are disposed with the element portion interposed therebetween range from 1 μm to 50 μm. This configuration enables the hysteresis to be further reduced.

In the current sensor according to the present invention, it is preferable that the ferromagnetic pinned layer of the magnetoresistive element be self-pinned in such a manner that a first ferromagnetic film and a second ferromagnetic film are coupled in an antiferromagnetic manner via an antiparallel coupling layer.

In this configuration, annealing in a magnetic field in the stripe width direction of the magnetoresistive element is not required in the manufacturing process of the magnetoresistive element. Therefore, the induced magnetic anisotropy in the stripe longitudinal direction which has been provided in the film formation process for the free magnetic layer can be preserved. Thus, the hysteresis can be reduced especially for an induction field in the stripe width direction which is to be detected.

DESCRIPTION OF THE PREFERRED EMBODIMENTS

Further improvement of measurement accuracy in a current sensor including magnetoresistive elements requires a reduced hysteresis in a magnetoresistive element, and also requires that the zero-field resistance values (R0) and the temperature coefficients of resistance (TCR0) in a zero magnetic field agree among the elements in a full-bridge circuit which is constituted by four elements such as magnetoresistive elements.

In a current sensor including magnetoresistive elements, a hard bias layer is formed to provide uniaxial anisotropy for a free magnetic layer, enabling reduction in hysteresis. In contrast, when a hard bias layer and a free magnetic layer are stacked one on top of the other, a contact portion which is in the free magnetic layer and with which the hard bias layer is in contact is strongly and firmly magnetized to form a dead zone for the external magnetic field. Therefore, this dead zone makes it difficult to reduce the hysteresis.

When a portion of a magnetoresistive element is removed to form a hard bias layer, the region in which the hard bias layer in the magnetoresistive element is formed does not function as a magnetoresistive element, resulting in parasitic resistance. Thus, when parasitic resistance occurs, there arises a problem in that the zero-field resistance values (R0) and the temperature coefficients of resistance (TCR0) in a zero magnetic field in the magnetoresistive elements constituting a full-bridge circuit may vary. In addition, this parasitic resistance increases as the number of hard bias layers is increased. Therefore, when the number of hard bias layers is increased to reduce the hysteresis sufficiently, the variation in the zero-field resistance values (R0) and the temperature coefficients of resistance (TCR0) in a zero magnetic field pronouncedly appears.

The inventors found that, in a current sensor including magnetoresistive elements, a hard bias layer formed in a removed portion obtained by removing a portion of a stripe-shaped magnetoresistive element enables reduction in the contact area between the hard bias layer and the free magnetic layer and reduction in the dead zone in the magnetoresistive element. In addition, the inventors found that, in the case where a hard bias layer is formed in a removed portion in the magnetoresistive element, an electrode layer which electrically connects adjacent magnetoresistive elements to each other is formed on the hard bias layer, whereby, even when multiple hard bias layers are formed, the adverse effect of the parasitic resistance caused by the hard bias layers can be reduced. Accordingly, the inventors devised the present invention.

An embodiment of the present invention will be described in detail below with reference to the attached drawings. In the description below, an embodiment in which a current sensor according to the present invention is applied to a magnetic balance current sensor (closed loop current sensor) will be described. Alternatively, a current sensor according to the present invention may be applied to a magnetic proportional current sensor (open loop current sensor) which measures a measurement current from the outputs of two magnetoresistive elements which are proportional to the induction field.

Figure 1:
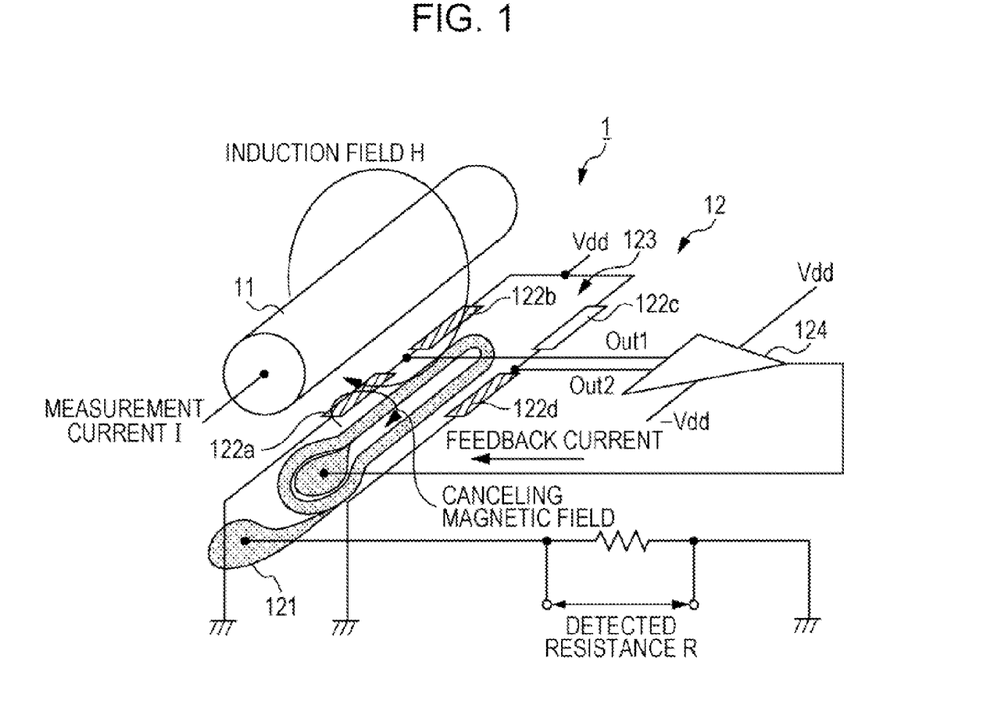
FIG. 1 is a schematic perspective view of a current sensor according to an embodiment of the present invention.
Figure 2:
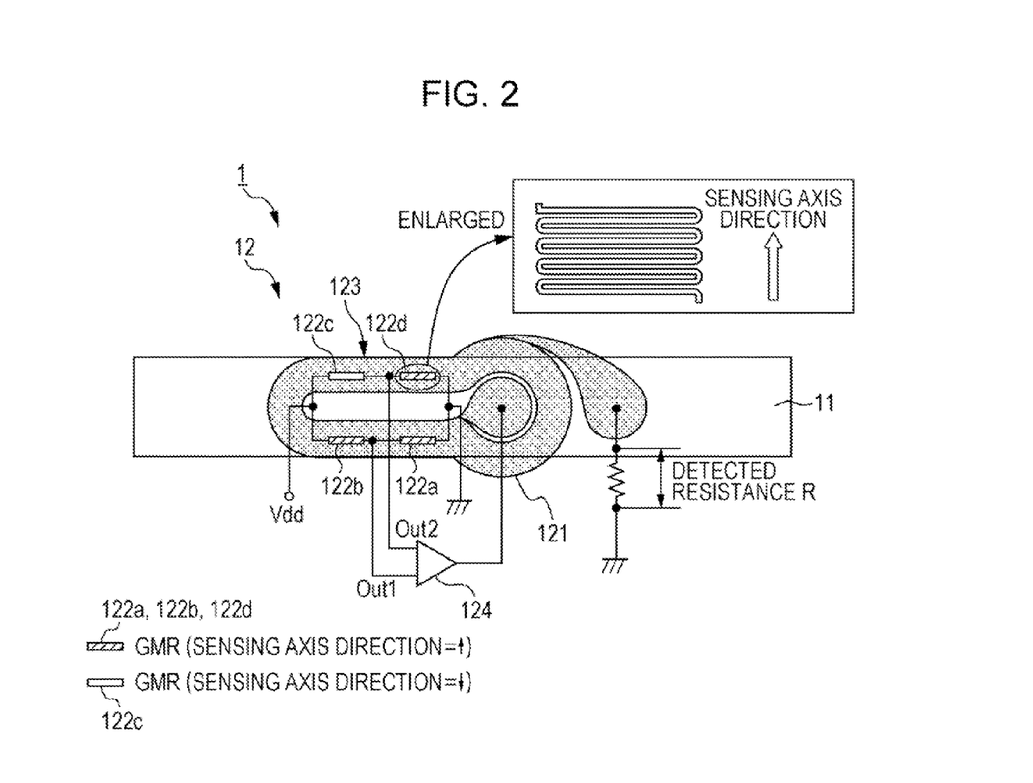
FIG. 2 is a schematic plan view of a current sensor according to an embodiment of the present invention.

FIG. 1 is a schematic perspective view of a current sensor 1 according to the present embodiment. FIG. 2 is a schematic plan view of the current sensor 1 according to the present embodiment. As illustrated in FIGS. 1 and 2, the current sensor 1 according to the present embodiment is disposed near a conductor 11 through which a measurement current I flows. The current sensor 1 includes a feedback circuit 12 which causes occurrence of a magnetic field (i.e., a canceling magnetic field) which cancels the induction field H caused by the measurement current I flowing through the conductor 11. The feedback circuit 12 includes a feedback coil 121 which is wound in a direction in which the magnetic field caused by the measurement current I is canceled, and four magnetoresistive elements 122a to 122d.

The feedback coil 121 is formed of a planar coil. This configuration includes no magnetic cores, achieving low-cost manufacture of the feedback coil 121. In addition, compared with a toroidal coil, the canceling magnetic field caused by the feedback coil 121 is prevented from spreading over a wide range, enabling avoidance of an adverse effect on peripheral circuits. Further, compared with a toroidal coil, in the case where the measurement current I is an alternating current, the canceling magnetic field caused by the feedback coil 121 is easy to control, and a current which is generated for the control is not so large. These effects become larger as the frequency of the measurement current I that is an alternating current is higher. In the case where the feedback coil 121 is formed of a planar coil, it is preferable to form a planar coil in such a manner that both of the induction field H and the canceling magnetic field appear in a plane which is parallel to the plane in which the planar coil is formed.

The resistance values of the magnetoresistive elements 122a to 122d are changed due to the application of the induction field H caused by the measurement current I. These four magnetoresistive elements 122a to 122d constitute a magnetic-field detection bridge circuit 123. Thus, use of the magnetic-field detection bridge circuit 123 having the magnetoresistive elements 122a to 122d achieves a highly sensitive current sensor 1.

The magnetic-field detection bridge circuit 123 has two outputs which cause a voltage difference according to the induction field H caused by the measurement current I. In the magnetic-field detection bridge circuit 123 illustrated in FIG. 2, a power supply Vdd is connected at a connection point between the magnetoresistive elements 122b and 122c, and a ground (GND) is connected at a connection point between the magnetoresistive elements 122a and 122d. Furthermore, in the magnetic-field detection bridge circuit 123, one output (Out1) is obtained from a connection point between the magnetoresistive elements 122a and 122b, and another output (Out2) is obtained from a connection point between the magnetoresistive elements 122c and 122d. These two outputs are amplified in an amplifier 124, and are supplied to the feedback coil 121 as a current (feedback current). The feedback current corresponds to a voltage difference according to the induction field H. At that time, a canceling magnetic field which cancels the induction field H occurs in the feedback coil 121. The measurement current I is measured by a detection unit (detected resistance R) on the basis of a current which flows through the feedback coil 121 when an equilibrium state in which the induction field H and the canceling magnetic field cancel each other out is attained.

As illustrated in an enlarged view in FIG. 2, the magnetoresistive elements 122a to 122d each are preferably a magnetoresistive element having a shape (meandering shape) in which multiple long strips (stripes) which are disposed so as to be oriented in the longitudinal direction and to be parallel to each other are connected at the ends with connecting portions. In this meandering shape, the sensing axis direction (Pin direction) is the direction, i.e., the stripe width direction D2 (see FIG. 3), which is perpendicular to the longitudinal direction of the long strips, i.e., the stripe longitudinal direction D1 (see FIG. 3). In addition, the induction field H and the canceling magnetic field are applied in the stripe width direction D2 which is perpendicular to the stripe longitudinal direction D1 in the meandering shape.

As illustrated in FIG. 1, in the current sensor 1 having such a configuration, the magnetoresistive elements 122a to 122d receive the induction field H caused by the measurement current I, and the induction field H is fed back so that the canceling magnetic field occurs from the feedback coil 121. Then, adequate adjustment is made so that two magnetic fields, i.e., the induction field H and the canceling magnetic field, cancel each other out and that the magnetic field for the magnetoresistive elements 122a to 122d is equal to zero.

The current sensor 1 having the above-described configuration uses the magnetic-field detection bridge circuit 123 having the magnetoresistive elements 122a to 122d, especially giant magneto resistance (GMR) elements or tunnel magneto resistance (TMR) elements, as a magnetic detection device. Thus, a highly sensitive current sensor 1 can be achieved. The current sensor 1 has the magnetic-field detection bridge circuit 123 constituted by the four magnetoresistive elements 122a to 122d having the same film structure. In the current sensor 1 having the above-described configuration, the feedback coil 121 and the magnetic-field detection bridge circuit 123 are formed on the same substrate, achieving reduction in size. Furthermore, the current sensor 1 has a configuration without a magnetic core, achieving reduction in size and cost.

In the current sensor 1 having the four magnetoresistive elements 122a to 122d disposed in the above-described manner, the canceling magnetic field is applied from the feedback coil 121 to the magnetoresistive elements 122a to 122d so that the voltage difference between the two outputs, i.e., Out1 and Out2, from the magnetic-field detection bridge circuit 123 is equal to zero. At that time, the value of a current flowing through the feedback coil 121 is detected, whereby the measurement current I is measured.

Figure 3:
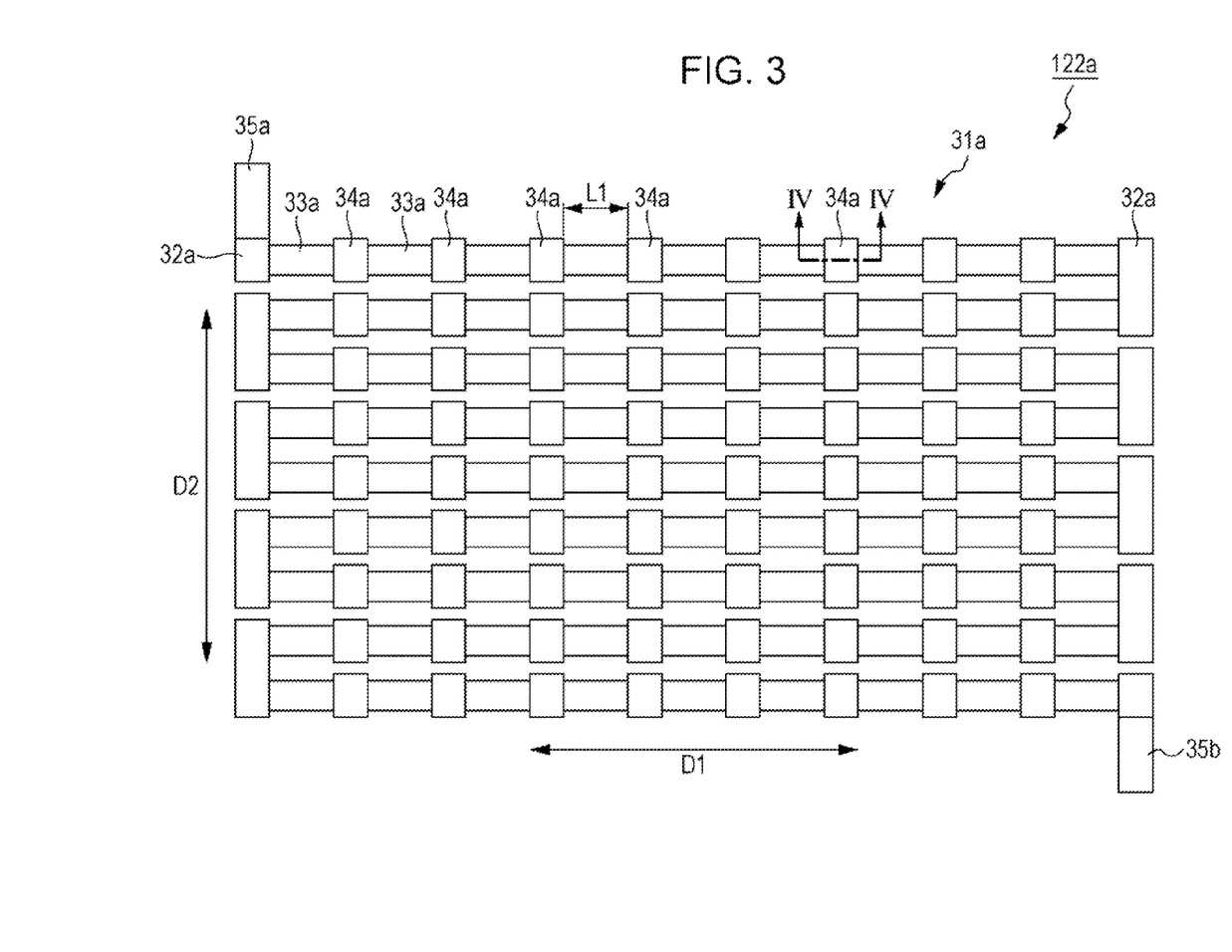
FIG. 3 is a schematic plan view of the element structure of a magnetoresistive element in a current sensor according to an embodiment of the present invention.
Figure 4:
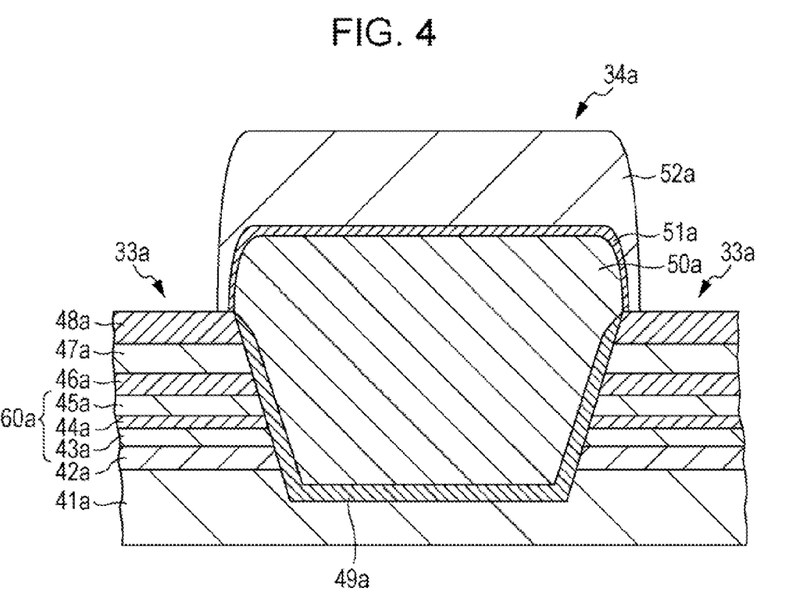
FIG. 4 is a schematic sectional view of the layered structure of a magnetoresistive element in a current sensor according to an embodiment of the present invention.

With reference to FIGS. 3 and 4, the element structure of the magnetoresistive elements 122a to 122d in the current sensor 1 according to the present embodiment will be described in detail. FIG. 3 is a schematic plan view of the element structure of the magnetoresistive element 122a in the current sensor 1 according to the present embodiment. FIG. 4 is a schematic sectional view of the layered structure of the magnetoresistive element 122a in the current sensor 1 according to the present embodiment. FIG. 4 is a section view taken along line IV-IV of FIG. 3. In the description below, the element structure will be described with the magnetoresistive element 122a taken as an example. The magnetoresistive elements 122b to 122d have a similar element structure.

As illustrated in FIG. 3, the magnetoresistive element 122a of the current sensor 1 has stripe-shaped (belt-like) long strips 31a which are disposed so as to be oriented in the stripe longitudinal direction D1 (hereinafter, also simply referred to as the "longitudinal direction D1") and to be parallel to each other. Each of the long strips 31a includes outer-side permanent magnet portions 32a (hereinafter, simply referred to as "permanent magnet portions 32a") which are disposed at the ends thereof, element portions 33a disposed so as to be spaced apart from each other in the longitudinal direction D1, and intermediate permanent magnet portions 34a (hereinafter, simply referred to as "permanent magnet portions 34a"), each of which is disposed between adjacent ones of the element portions 33a. The permanent magnet portions 34a are disposed so that hard bias layers 50a (see FIG. 4) described below are disposed at certain pitches L1 in the longitudinal direction D1 of the long strip 31a.

The ends of two long strips 31a which are adjacent to each other are connected with a permanent magnet portion 32a in the stripe width direction D2 (hereinafter, also simply referred to as the "width direction D2") which is perpendicular to the longitudinal direction D1 of the long strips 31a. A permanent magnet portion 32a is disposed so as to connect different long strips 31a to each other at the ends. In other words, among the long strips 31a disposed so as to be parallel to each other, the first and second long strips 31a from the top are connected with a permanent magnet portion 32a at one end (the right-side end) in the longitudinal direction D1, and the second and third long strips 31a from the top are connected with a permanent magnet portion 32a at the other end (the left-side end) in the longitudinal direction D1. Two adjacent long strips 31a are connected with a permanent magnet portion 32a at one end or the other end in an alternate manner.

In the magnetoresistive element 122a, one end is connected to a connector 35a via a permanent magnet portion 32a, and the other end is connected to a connector 35b via a permanent magnet portion 32a. The connectors 35a and 35b are connected to a calculation unit (not illustrated) which calculates the magnitude of the measurement current from the output signals from the magnetoresistive elements 122a to 122d. The magnetoresistive element 122a outputs an output signal to the calculation unit (not illustrated) via the connectors 35a and 35b.

The layered structure of the element portion 33a will be described. As illustrated in FIG. 4, the element portions 33a and the permanent magnet portions 34a in the magnetoresistive element 122a are formed on an aluminum oxide film 41a formed on a substrate (not illustrated) such as a silicon substrate. The element portions 33a are disposed in such a manner as to be spaced apart from each other at certain intervals, and a permanent magnet portion 34a is formed between adjacent ones of the element portions 33a. The aluminum oxide film 41a may be formed by, for example, sputtering. FIG. 4 illustrates the layered structure of an element portion 33a and a permanent magnet portion 34a. A permanent magnet portion 32a has a layered structure similar to that of the permanent magnet portion 34a.

The layered structure of an element portion 33a will be described. An element portion 33a includes a seed layer 42a, a first ferromagnetic film 43a, an antiparallel coupling layer 44a, a second ferromagnetic film 45a, a non-magnetic intermediate layer 46a, a free magnetic layer 47a, and a protective layer 48a which are stacked on top of one another in this sequence.

The seed layer 42a is composed of, for example, NiFeCr or Cr. The protective layer 48a is composed of, for example, Ta. In the above-described layered structure, an underlying layer composed of a non-magnetic material, for example, including at least one element from Ta, Hf, Nb, Zr, Ti, Mo, and W, may be formed between the substrate (not illustrated) and the seed layer 42a.

In the magnetoresistive element 122a, the first ferromagnetic film 43a and the second ferromagnetic film 45a are coupled via the antiparallel coupling layer 44a in an antiferromagnetic manner, forming a so-called self-pinned ferromagnetic pinned layer 60a (SFP: synthetic ferri pinned layer). Thus, by forming the self-pinned (bottom-spin-valve) magnetoresistive element 122a, annealing in a magnetic field which is necessary for a magnetoresistive element of the related art is not necessary in the manufacturing process for the magnetoresistive element 122a, enabling preserving of induced magnetic anisotropy in the stripe longitudinal direction D1 which is provided during the formation of the free magnetic layer 47a. This can reduce the hysteresis in the direction in which the detection is to be performed (stripe width direction D2).

In the ferromagnetic pinned layer 60a, the thickness of the antiparallel coupling layer 44a is set to 0.3 nm to 0.45 nm, or 0.75 nm to 0.95 nm, resulting in a strong antiferromagnetic coupling between the first ferromagnetic film 43a and the second ferromagnetic film 45a.

The magnetization amount (Ms·t) of the first ferromagnetic film 43a is substantially the same as that of the second ferromagnetic film 45a. That is, the difference between the magnetization amounts of the first ferromagnetic film 43a and the second ferromagnetic film 45a is substantially equal to zero. Thus, an effective anisotropy field for the ferromagnetic pinned layer is large. Therefore, sufficient magnetization stability for the ferromagnetic pinned layer 60a can be achieved without using an antiferromagnetic material. This is because the effective anisotropy field for an SFP layer is expressed in Expression (1) described below, where the film thickness of the first ferromagnetic film 43a is represented by t1, the film thickness of the second ferromagnetic film 45a is represented by t2, and the magnetization per unit volume and the induced magnetic anisotropy constant of both of the layers are represented by Ms and K, respectively. Therefore, the magnetoresistive element 122a used in the current sensor 1 according to the present embodiment has a film structure having no antiferromagnetic layers.

$$\text{eff } Hk = 2(K \cdot t1 + K \cdot t2)/(Ms \cdot t1 - Ms \cdot t2) \qquad \text{Expression (1)}$$

The Curie temperature (Tc) of the first ferromagnetic film 43a is substantially the same as that of the second ferromagnetic film 45a. Thus, the difference between the magnetization amounts (Ms·t) of the first ferromagnetic film 43a and the second ferromagnetic film 45a is substantially equal to zero even at high temperatures, enabling high magnetization stability to be preserved.

The first ferromagnetic film 43a is preferably composed of a CoFe alloy including Fe of 40 at % to 80 at %. This is because a CoFe alloy having this composition range has a large coercivity and can hold a stable magnetization for the external magnetic field. The second ferromagnetic film 45a is preferably composed of a CoFe alloy including Fe of 0 at % to 40 at %. This is because a CoFe alloy having this composition range has a small coercivity and is easy to be magnetized in the antiparallel direction (the opposite direction) with respect to the direction in which the first ferromagnetic film 43a is preferentially magnetized. As a result, Hk in Expression (1) described above can be made larger. In addition, by limiting the second ferromagnetic film 45a to a film having this composition range, the resistance change ratio of the magnetoresistive element 122a can be made large.

It is preferable that a magnetic field be applied to the first ferromagnetic film 43a and the second ferromagnetic film 45a in the stripe width direction D2 in the meandering shape during the film formation process and that induced magnetic anisotropy be provided for the first ferromagnetic film 43a and the second ferromagnetic film 45a after the film formation process. Thus, the first ferromagnetic film 43a and the second ferromagnetic film 45a are magnetized in the stripe width direction D2 in an antiparallel manner. In addition, the magnetization directions of the first ferromagnetic film 43a and the second ferromagnetic film 45a depend on the direction of a magnetic field applied during the formation of the first ferromagnetic film 43a. Accordingly, by changing the direction of a magnetic field applied during the formation of the first ferromagnetic film 43a, multiple magnetoresistive elements 122a having ferromagnetic pinned layers 60a whose magnetization directions are different from each other can be formed on the same substrate.

The antiparallel coupling layer 44a in the ferromagnetic pinned layer 60a is composed of, for example, Ru. The free magnetic layer (free layer) 47a is composed of a magnetic material such as a CoFe alloy, a NiFe alloy, or a CoFeNi alloy. The non-magnetic intermediate layer 46a is composed of, for example, Cu. It is preferable that a magnetic field be applied to the free magnetic layer 47a in the stripe longitudinal direction D1 in the meandering shape during the film formation process, and that induced magnetic anisotropy be provided for the free magnetic layer 47a after the film formation process. Thus, the resistance of a magnetoresistive element is linearly changed for the external magnetic field in the stripe width direction D2 (the magnetic field from the measurement current), resulting in a small hysteresis. The magnetoresistive element described above has a spin-valve structure including the ferromagnetic pinned layer 60a, the non-magnetic intermediate layer 46a, and the free magnetic layer 47a.

An example of the film structure of the magnetoresistive element 122a used in the current sensor 1 according to the present embodiment is as follows: NiFeCr (the seed layer 42a: 5 nm)/Fe70Co30 (the first ferromagnetic film 43a: 1.65 nm)/Ru (the antiparallel coupling layer 44a: 0.4 nm)/Co90Fe10 (the second ferromagnetic film 45a: 2 nm)/Cu (the non-magnetic intermediate layer 46a: 2.2 nm)/Co90Fe10 (the free magnetic layer 47a: 1 nm)/Ni81Fe19 (the free magnetic layer 47a: 7 nm)/Ta (the protective layer 48a: 5 nm).

The layered structure of a permanent magnet portion 34a will be described. In the current sensor 1 according to the present embodiment, a permanent magnet portion 34a is disposed in a region in which a portion of an element portion 33a disposed so as to cover the aluminum oxide film 41a is removed by, for example, etching.

A permanent magnet portion 34a includes an underlying layer 49a formed on the aluminum oxide film 41a and element portions 33a, a hard bias layer 50a formed on the underlying layer 49a, a diffusion barrier layer 51a formed on the hard bias layer 50a, and an electrode layer 52a formed on the diffusion barrier layer 51a.

The underlying layer 49a is composed of an alloy including Ta/CrTi. The underlying layer 49a is formed in a region including a contact portion between the hard bias layer 50a and the free magnetic layer 47a of an element portion 33a, and reduces the bias magnetic field from the hard bias layer 50a to the free magnetic layer 47a of the element portion 33a. Thus, by forming the underlying layer 49a, the hard bias layer 50a and the free magnetic layer 47a are not directly in contact with each other. Therefore, the state in which the magnetization direction is pinned in the contact portion in the free magnetic layer 47a between the free magnetic layer 47a and the hard bias layer 50a is suppressed, resulting in a reduced dead zone in the free magnetic layer 47a. Thus, the hysteresis can be reduced.

The hard bias layer 50a is composed of, for example, CoPt or CoCrPt, and applies a bias magnetic field to the free magnetic layer 47a of the element portion 33a. In the current sensor 1 according to the present embodiment, a permanent magnet portion 34a is formed by stacking layers on top of one another in such a manner that the bottom surface of the hard bias layer 50a is disposed at a height position which is located in the aluminum oxide film 41a of the element portion 33a (a position under the bottom surface of the seed layer 42a) and that the top surface of the hard bias layer 50a is disposed at a height position which is located above the top surface of the protective layer 48a of the element portion 33a. Thus, by forming the hard bias layer 50a in such a manner that the hard bias layer 50a covers a region including the side of the free magnetic layer 47a, a bias magnetic field can be applied in a direction which is substantially perpendicular to the sensing axis direction of the free magnetic layer 47a. This enables the hysteresis to be effectively reduced.

The diffusion barrier layer 51a is formed so as to cover the hard bias layer 50a. The diffusion barrier layer 51a is composed of, for example, Ta.

The electrode layer 52a is composed of, for example, Au, Al, Cu, or Cr, and is formed so as to cover the diffusion barrier layer 51a. The electrode layer 52a is formed so as to be in contact with the protective layers 48a of the element portions 33a that are disposed on both the sides of the permanent magnet portion 34a in the longitudinal direction D1 of the long strip 31a, and electrically connects the element portions 33a that are disposed on both the sides of the permanent magnet portion 34a.

In the current sensor 1 according to the present embodiment, an electrode layer 52a is provided for a permanent magnet portion 34a, and electrically connects the element portions 33a that are adjacent to each other. Accordingly, an output signal is output from the magnetoresistive element 122a via the electrode layers 52a. Thus, by outputting an output signal of the magnetoresistive element 122a via the electrode layers 52a, an adverse effect of parasitic resistance caused by the hard bias layer 50a of a permanent magnet portion 34a having the fixed magnetization direction can be reduced, enabling variation in element resistances to be suppressed.

In the current sensor 1 according to the present embodiment, a pitch L1 between the hard bias layers 50a in the longitudinal direction D1 of the magnetoresistive element 122a is preferably set to 1 μm to 50 μm. By setting a pitch L1 between the hard bias layers 50a to 1 μm to 50 μm, the hysteresis of the magnetoresistive element 122a can be reduced.

In the current sensor 1 according to the present embodiment, the width of a stripe in the sensing axis direction (stripe width direction D2) of the magnetoresistive element 122a preferably ranges from 2 μm to 9 μm. When the width of a stripe is within the range of 2 μm to 9 μm, the hysteresis is reduced, and the linearity of the output signal of the magnetoresistive element 122a is improved. In addition, in consideration of the linearity, the magnetoresistive element 122a is desirably formed in such a manner that the longitudinal direction D1 of a long strip 31a is perpendicular to both of the direction of the induction field H and the direction of the canceling magnetic field.

Figure 5:
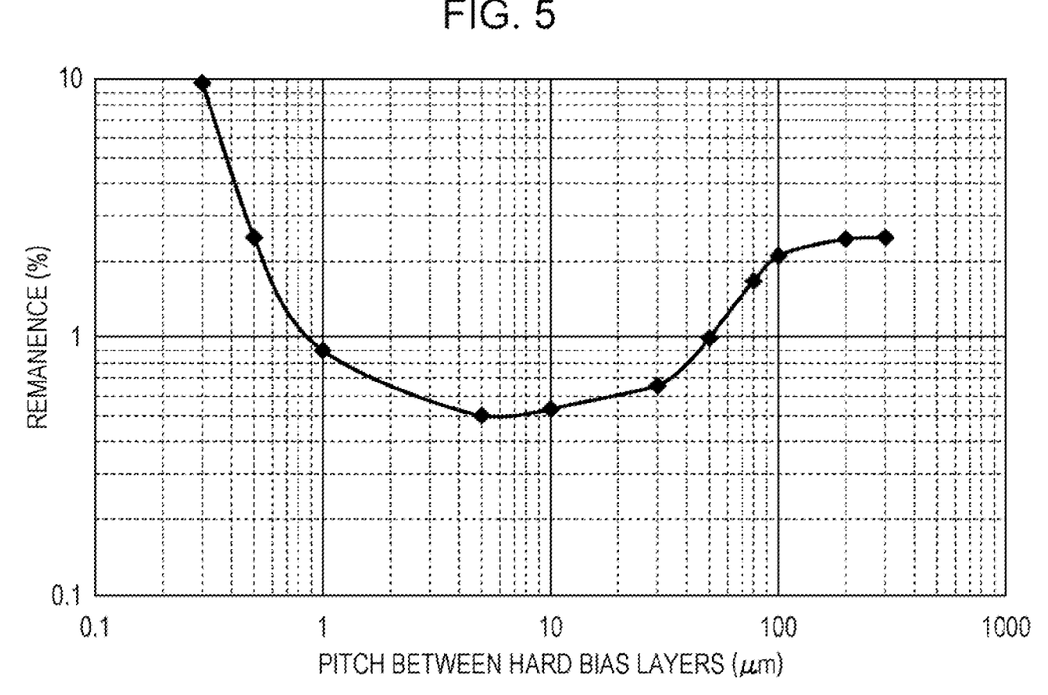
FIG. 5 is a diagram illustrating the relationship between the remanence and the pitch between hard bias layers in a current sensor according to an embodiment of the present invention.
Figure 6:
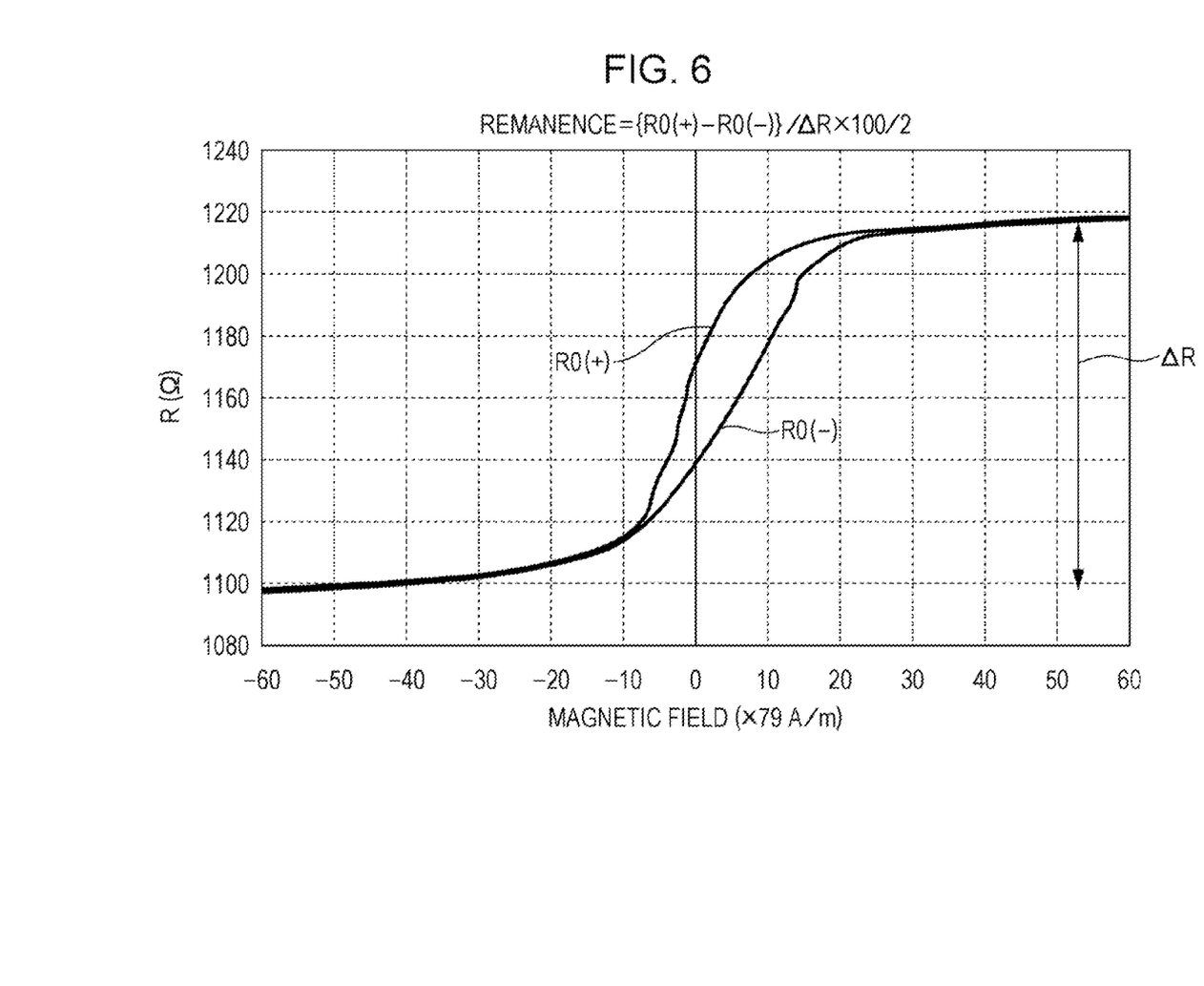
FIG. 6 is a diagram illustrating the definition of remanence in a current sensor according to an embodiment of the present invention.

Using the current sensor 1 having the above-described configuration, the relationship between the pitch L1 between the hard bias layers 50a and the remanence was investigated. The results are illustrated in FIG. 5. In the example in FIG. 5, the stripe width of a long strip 31a was fixed to a predetermined value, and the remanence was measured while the pitch L1 between the hard bias layers 50a was being changed. As illustrated in FIG. 6, a remanence is represented in a ratio of a value obtained by subtracting a resistance value (R0(−)) obtained when the magnetic field is returned to zero from a negative, from a resistance value (R0(+)) obtained when the magnetic field is returned to zero from a positive, to a difference (ΔR) between the resistance values for the magnetoresistive element 122a. A small remanence is preferable because the hysteresis is small. A remanence was calculated by measuring a change in the resistance value of the magnetoresistive element 122a with respect to the external magnetic field.

As is clear from FIG. 5, as the pitch L1 between the hard bias layers 50a is increased from 0.3 µm, the remanence decreases. When the pitch L1 between the hard bias layers 50a is equal to or larger than 1 µm, the remanence becomes equal to or less than 1%. The remanence is minimized when the pitch L1 between the hard bias layers 50a is equal to 5 µm. When the pitch L1 exceeds 5 µm, the remanence increases. When the pitch L1 between the hard bias layers 50a is equal to or larger than 50 µm, the remanence becomes equal to or larger than 1%. Thus, in the current sensor 1 according to the present embodiment, the remanence is equal to or less than 1% when the pitch L1 between the hard bias layers 50a is equal to or larger than 1 µm and is equal to or less than 50 µm. Thus, it is apparent that the hysteresis is significantly reduced.

Figure 7:
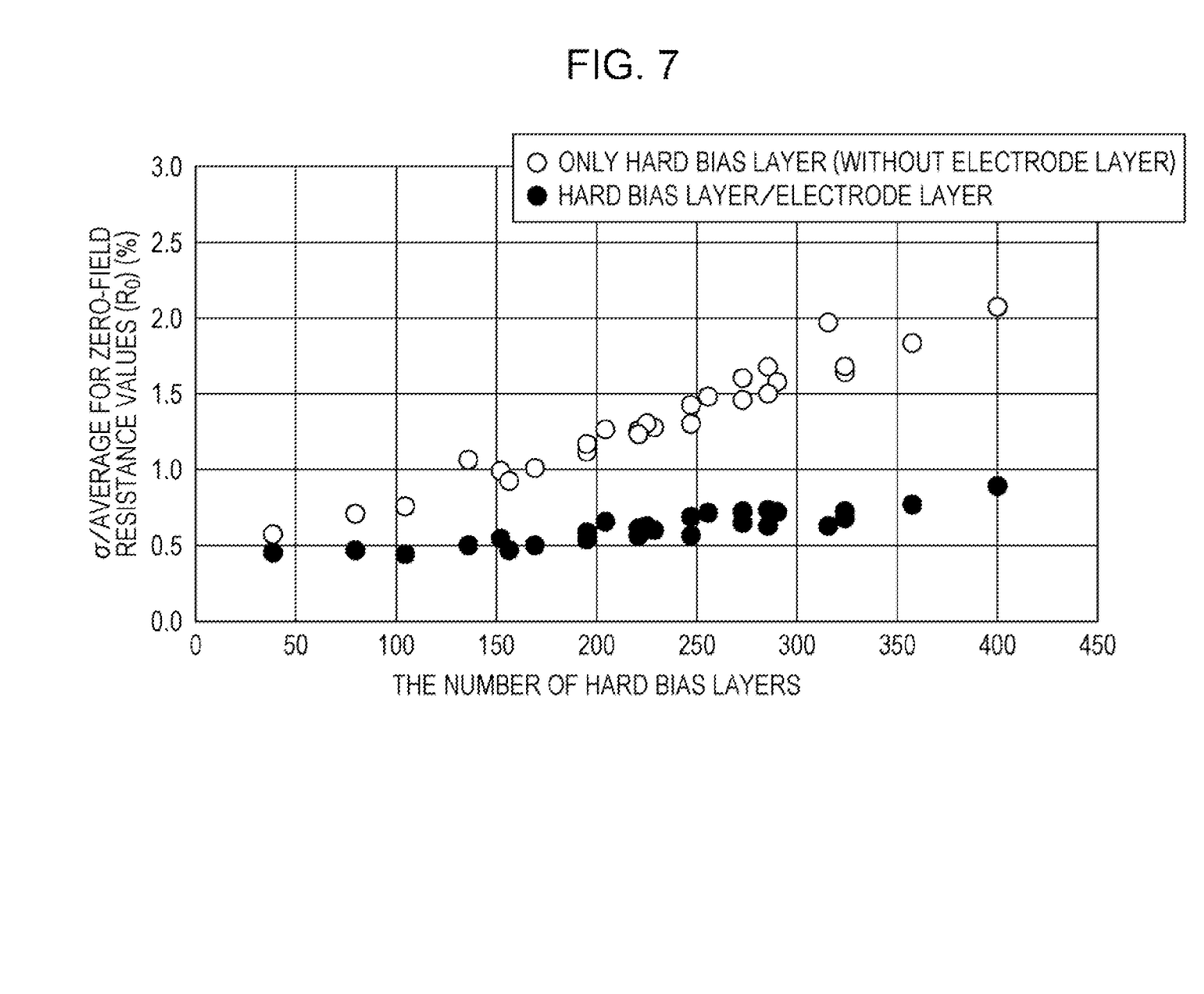
FIG. 7 is a diagram illustrating the relationship between a ratio of the standard deviation σ to the average for zero-field resistance values (R0) and the number of permanent magnet portions in a current sensor according to an embodiment of the present invention.

The effect of the electrode layer 52a in the magnetoresistive element 122a was investigated. The results are illustrated in FIG. 7. In the example illustrated in FIG. 7, the current sensor 1 according to the above-described embodiment in which permanent magnet portions 32a and 34a each are provided with an electrode layer 52a, and a current sensor according to a comparative example in which permanent magnet portions 32a and 34a each are not provided with an electrode layer 52a were used to measure a ratio of the standard deviation σ to the average for the zero-field resistance values (R0) of a full-bridge circuit which was obtained when the number of hard bias layers 50a in the magnetoresistive element 122a was changed. In FIG. 7, 224 magnetoresistive elements were used for the measurement for each of the current sensors, and the evaluation was made.

As is clear from FIG. 7, in the current sensor 1 according to the present embodiment, when the number of permanent magnet portions 32a and 34a in the magnetoresistive element 122a is about 40, the value σ/average for zero-field resistance values (R0) is of the order of about 0.5%. As the number of permanent magnet portions 32a and 34a in the magnetoresistive element 122a is increased, the value σ/average for zero-field resistance values (R0) slightly increases. When the number of permanent magnet portions 32a and 34a is about 400, the value σ/average for zero-field resistance values (R0) reaches about 0.9%.

In contrast, in the current sensor according to a comparative example in which permanent magnet portions 32a and 34a in the magnetoresistive element 122a each are not provided with an electrode layer 52a, when the number of permanent magnet portions 32a and 34a is about 40, the value σ/average for zero-field resistance values (R0) is about 0.6%. When the number of permanent magnet portions 32a and 34a is about 400, the value σ/average for zero-field resistance values (R0) significantly increases up to about 2.1%.

Thus, in the current sensor 1 according to the present embodiment, by providing the permanent magnet portions 32a and 34a with the electrode layer 52a, even when the number of permanent magnet portions 32a and 34a is increased, an increase in the value σ/average for zero-field resistance values (R0) can be significantly suppressed. Therefore, by disposing multiple permanent magnet portions 32a and 34a and applying a magnetic field to the free magnetic layer 47a in each of the element portions 33a, variation in the zero-field resistance values (R0) of the magnetoresistive elements 122a to 122d can be suppressed, enabling the hysteresis to be significantly reduced.

Figure 8:
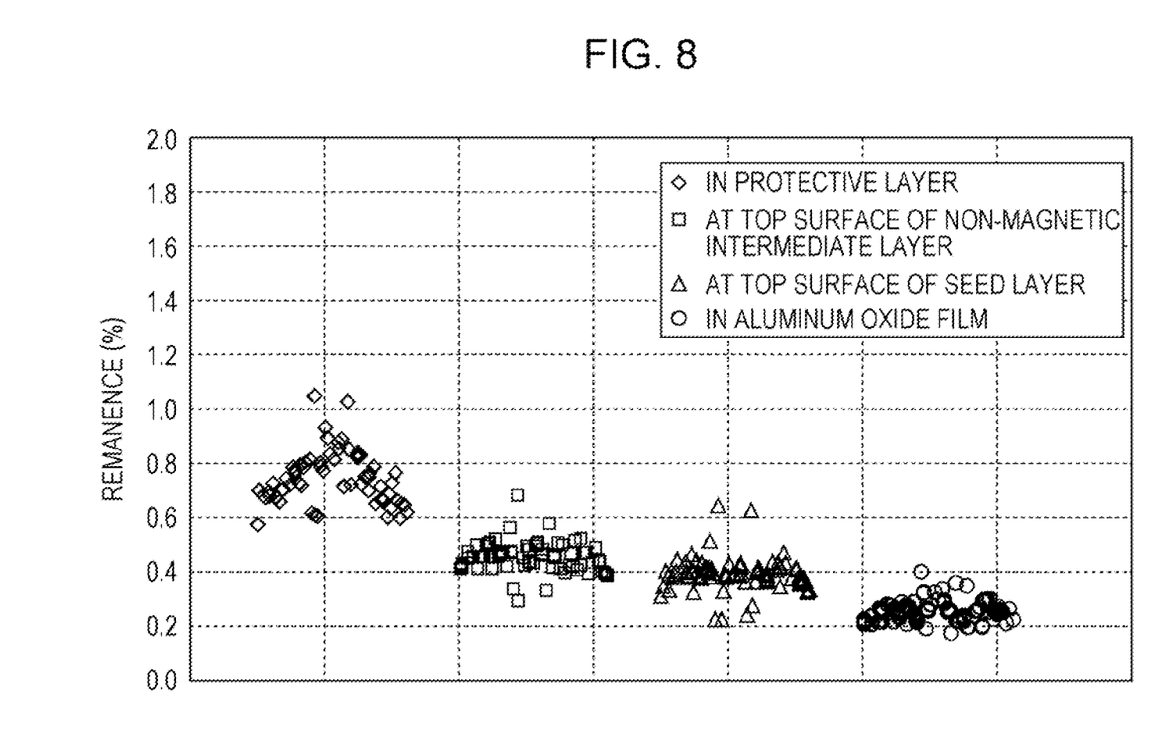
FIG. 8 is a diagram illustrating the relationship between the remanence and the positional relationship between an element portion and the hard bias layer of a permanent magnet portion in a current sensor according to an embodiment of the present invention.

The correlation between the layered structure and the remanence for the permanent magnet portions 32a and 34a in the magnetoresistive element 122a of the current sensor 1 according to the above-described embodiment was investigated. The results are illustrated in FIG. 8. In the example illustrated in FIG. 8, the remanence was measured under the condition that an etching amount for an element portion 33a which is used when the permanent magnet portions 32a and 34a are formed was changed in the layered structure illustrated in FIG. 4 so that the height position of the bottom surface of the hard bias layer 50a was changed with respect to each layer in the element portion 33a. FIG. 8 illustrates the following cases: the case where the bottom surface of the hard bias layer 50a is disposed at the mid-height position of the protective layer 48a of an element portion 33a (represented by rhombus plots); the case where the bottom surface of the hard bias layer 50a is disposed at the height position at which the top surface of the non-magnetic intermediate layer 46a is located (represented by rectangle plots); the case where the bottom surface of the hard bias layer 50a is disposed at the height position at which the top surface of the seed layer 42a is located (represented by triangle plots); and the case where the bottom surface of the hard bias layer 50a is disposed at a height position which is located in the aluminum oxide film 41a, i.e., below the bottom surface of the seed layer 42a, (represented by circle plots).

As is clear from FIG. 8, when the bottom surface of the hard bias layer 50a is disposed at a height position which is located in the protective layer 48a, the remanence is about 0.8%. When the bottom surface of the hard bias layer 50a is disposed at the height position at which the top surface of the non-magnetic intermediate layer 46a is located, the remanence is about 0.5%. When the bottom surface of the hard bias layer 50a is disposed at the height position at which the top surface of the seed layer 42a is located, the remanence is about 0.4%. When the bottom surface of the hard bias layer 50a is disposed at a height position which is located in the aluminum oxide film 41a, the remanence is about 0.3%. Thus, in the current sensor 1 according to the present embodiment, it is found that, as the bottom surface of the hard bias layer 50a is located at a lower position with respect to an element portion 33a, the remanence becomes smaller.

As described above, in the current sensor 1 according to the above-described embodiment, each of the permanent magnet portions 32a and 34a is provided with the hard bias layer 50a, and a bias magnetic field is applied from the hard bias layer 50a to a free magnetic layer 47a, enabling the hysteresis of the magnetoresistive element 122a to be reduced. By forming the electrode layer 52a so as to cover the hard bias layer 50a in each of the permanent magnet portions 32a and 34a, a current flowing through an element portion 33a is diverted via the electrode layer 52a, enabling the parasitic resistance for the magnetoresistive element 122a to be reduced. Thus, variation in the zero-field resistance values (R0) and the temperature coefficients of resistance (TCR0) in a zero magnetic field among the magnetoresistive elements 122a to 122d constituting a full-bridge circuit can be reduced, enabling the measurement accuracy to be improved.

In the current sensor 1 according to the above-described embodiment, by forming the underlying layer 49a between an element portion 33a and the hard bias layer 50a, the hard bias layer 50a and the free magnetic layer 47a are in contact with each other via the underlying layer 49a. Therefore, a dead zone which is in the free magnetic layer 47a of an element portion 33a and which is caused by the bias magnetic field from the hard bias layer 50a can be reduced, resulting in a reduced hysteresis.

In the current sensor 1 according to the present embodiment, each of the permanent magnet portions 32a and 34a is formed in a region in which a portion of an element portion 33a in the magnetoresistive element 122a is removed. Thus, a bias magnetic field can be applied from the hard bias layer 50a in the direction perpendicular to the sensing axis direction of the free magnetic layer 47a, enabling uniaxial anisotropy to be provided for the free magnetic layer 47a and enabling the hysteresis to be further reduced.

The present invention is not limited to the above-described embodiment, and various modifications can be made and embodied. For example, the materials, the connection relationship between elements, the thickness, the size, and the manufacturing method in the above-described embodiment may be changed as appropriate and embodied. In addition to these, various modifications may be made in appropriate without departing from the scope of the present invention.

The present invention has an effect that the hysteresis of a magnetoresistive element can be reduced and that the measurement accuracy is improved. In particular, the present invention can be applied to a current sensor which detects the magnitude of a current for driving a motor in an electric car.

What is claimed is:

1. A current sensor comprising:
    a magnetoresistive element formed in a stripe shape, the magnetoresistive element having a sensing axis in a certain direction, the magnetoresistive element including:
        a plurality of element portions disposed so as to be spaced apart from each other in a longitudinal direction of the stripe shape; and
        a plurality of permanent magnet portions, each disposed between adjacent ones of the plurality of element portions,
    wherein each of the plurality of element portions has a layered structure including:
        a free magnetic layer whose magnetization direction is changed with respect to an external magnetic field applied thereto;
        a non-magnetic intermediate layer; and
        a ferromagnetic pinned layer whose magnetization direction is pinned, and
    wherein the permanent magnet portion includes:
        a hard bias layer that applies a bias magnetic field to the free magnetic layer; and
        an electrode layer disposed so as to cover the hard bias layer, the electrode layer electrically connecting adjacent ones of the plurality of element portions.

2. The current sensor according to claim 1, wherein the magnetoresistive element further includes:
    an underlying layer disposed between the hard bias layer of the permanent magnet portion and the free magnetic layer of the element portion.

3. The current sensor according to claim 1, wherein the hard bias layer of the permanent magnet portion is disposed in a region in which the ferromagnetic pinned layer, the non-magnetic intermediate layer, and the free magnetic layer in the element portion of the magnetoresistive element are removed.

4. The current sensor according to claim 1, wherein the magnetoresistive element includes a plurality of belt-like strips oriented in the longitudinal direction of the stripe shape, the strips being parallel to each other and connected to connecting portions at respective ends so as to form a meandering shape.

5. The current sensor according to claim 1, wherein the stripe shape has a width ranging from 2 μm to 9 μm.

6. The current sensor according to claim 1, wherein a pitch between the hard bias layers of the plurality of permanent magnet portions ranges from 1 μm to 50 μm.

7. The current sensor according to claim 1, wherein the ferromagnetic pinned layer is a self-pinned type, including:
    a first ferromagnetic film;
    a second ferromagnetic film; and
    an antiparallel coupling layer interposed therebetween, the first and second ferromagnetic films being coupled in an antiferromagnetic manner via the antiparallel coupling layer.

8. The current sensor according to claim 1, wherein the element portions and the permanent magnet portions are alternately disposed to form the strip shape of the magnetoresistive element.

9. A current sensor comprising:
    a magnetoresistive element formed in a plurality of belt-like strips parallel to each other and extending in a longitudinal direction, adjacent ones of the plurality of strips being connected to connecting portions at respective ends such that the plurality of strips form a meandering shape, the magnetoresistive element having a sensing axis in a certain direction, the magnetoresistive element including:
        a plurality of element portions disposed so as to be spaced apart from each other in the longitudinal direction;
        a plurality of permanent magnet portions, each disposed between adjacent ones of the plurality of element portions; and
    wherein each of the plurality of element portions has a layered structure including:
        a free magnetic layer whose magnetization direction is changed with respect to an external magnetic field applied thereto;
        a non-magnetic intermediate layer; and
        a ferromagnetic pinned layer whose magnetization direction is pinned, and
    wherein the permanent magnet portion includes:
        a hard bias layer that applies a bias magnetic field to the free magnetic layer; and
        an electrode layer disposed so as to cover the hard bias layer, the electrode layer electrically connecting adjacent ones of the plurality of element portions.

10. A current sensor comprising:
    a magnetoresistive element formed in a stripe shape, the magnetoresistive element having a sensing axis in a certain direction, the magnetoresistive element including:
        a plurality of element portions disposed so as to be spaced apart from each other in a longitudinal direction of the stripe shape; and
        a plurality of permanent magnet portions, each disposed between adjacent ones of the plurality of element portions,
    wherein each of the plurality of element portions has a layered structure including:
        a free magnetic layer whose magnetization direction is changed with respect to an external magnetic field applied thereto;
        a non-magnetic intermediate layer; and
        a ferromagnetic pinned layer whose magnetization direction is pinned,
    wherein each of the permanent magnet portions includes:
        a hard bias layer that applies a bias magnetic field to the free magnetic layer; and
        an electrode layer disposed so as to cover the hard bias layer, the electrode layer electrically connecting adjacent ones of the plurality of element portions, and wherein a pitch between the hard bias layers of the plurality of permanent magnet portions ranges from 1 μm to 50 μm.

11. A current sensor comprising:
a magnetoresistive element formed in a stripe shape, the magnetoresistive element having a sensing axis in a certain direction, the magnetoresistive element including:
   a plurality of element portions disposed so as to be spaced apart from each other in a longitudinal direction of the stripe shape; and
   a plurality of permanent magnet portions, each disposed between adjacent ones of the plurality of element portions,
wherein each of the plurality of element portions has a layered structure including:
   a free magnetic layer whose magnetization direction is changed with respect to an external magnetic field applied thereto;
   a non-magnetic intermediate layer; and
   a ferromagnetic pinned layer whose magnetization direction is pinned,
wherein the permanent magnet portion includes:
   a hard bias layer that applies a bias magnetic field to the free magnetic layer; and
   an electrode layer disposed so as to cover the hard bias layer, the electrode layer electrically connecting adjacent ones of the plurality of element portions, and
wherein the ferromagnetic pinned layer is a self-pinned type, including:
   a first ferromagnetic film;
   a second ferromagnetic film; and
   an antiparallel coupling layer interposed therebetween, the first and second ferromagnetic films being coupled in an antiferromagnetic manner via the antiparallel coupling layer.

* * * * *